United States Patent

Feurstein et al.

[11] Patent Number: 5,922,605
[45] Date of Patent: Jul. 13, 1999

[54] POLYMERIZATION APPARATUS AND METHOD FOR CONTROLLING POLYMERIZATION APPARATUS

[75] Inventors: Markus Feurstein, Feldkirch-Tosters, Australia; Jurgen Mertins, Gams, Switzerland

[73] Assignee: Ivoclar AG, Schaan, Liechtenstein

[21] Appl. No.: 08/850,080

[22] Filed: May 2, 1997

[30] Foreign Application Priority Data

May 8, 1996 [DE] Germany ............... 196 18 542

[51] Int. Cl.⁶ ............. G01N 35/08; A61C 13/08; F21S 3/00
[52] U.S. Cl. ............ 436/55; 250/492.1; 250/455.11; 250/504 R; 264/19; 362/218; 362/219; 422/62; 422/109; 433/29; 436/85
[58] Field of Search ............... 436/85, 55; 250/492.1, 250/453.11, 504 H, 504 R, 455.11; 433/29, 215; 264/19; 362/225, 219, 218; 422/62, 109

[56] References Cited

U.S. PATENT DOCUMENTS

| | | | |
|---|---|---|---|
| 4,546,261 | 10/1985 | Gonser et al. | 250/492.1 |
| 4,571,665 | 2/1986 | Herold et al. | 362/225 |
| 4,890,997 | 1/1990 | Beins et al. | 425/174 |
| 5,040,964 | 8/1991 | Oppawsky et al. | 425/135 |
| 5,135,685 | 8/1992 | Masuhara et al. | 264/22 |
| 5,135,686 | 8/1992 | Masuhara et al. | 264/22 |
| 5,348,475 | 9/1994 | Waknine et al. | 433/215 |
| 5,554,855 | 9/1996 | Ueno | 250/455.11 |

FOREIGN PATENT DOCUMENTS

| | | |
|---|---|---|
| 82 09 544 U1 | 2/1983 | Germany . |
| 86 27 655 U1 | 4/1987 | Germany . |
| 3825055 | 1/1990 | Germany . |
| 39 10 438 C2 | 10/1990 | Germany . |
| 94 02 179 U1 | 9/1994 | Germany . |
| 3-55212 | 3/1991 | Japan . |
| 8-173460 | 7/1996 | Japan . |

*Primary Examiner*—Arlen Soderquist
*Attorney, Agent, or Firm*—John C. Thompson; Alan S. Korman

[57] ABSTRACT

A polymerization apparatus includes a support plate for supporting a workpiece to be polymerized and a hood comprising a light source for guiding light to the workpiece such that the light impinges on at least two sides of the workpiece. The hood is liftable relative to the support plate so as to allow access to the workpiece when in a lifted position. A heat source for heating the workpiece is provided. A control device controls the function of the polymerization apparatus. A method for operating the polymerization apparatus includes the steps of heating the workpiece to a desired temperature after switching on the light source, maintaining the desired temperature for a desired polymerization cycle time period, and subsequently shutting down the light source and the heat source for a final polymerization cycle time period.

20 Claims, 2 Drawing Sheets

POLYMERIZATION APPARATUS AND METHOD FOR CONTROLLING POLYMERIZATION APPARATUS

BACKGROUND OF THE INVENTION

The invention relates to a polymerization apparatus and a method for controlling the polymerization apparatus. The polymerization apparatus comprises a light source that guides light to a workpiece to be polymerized which is arranged on a support plate, whereby the light of the light source impinges on at least two sides of the workpiece. The apparatus also comprises a heat source for the workpiece and a control device.

A polymerization apparatus is, for example, known from German Gebrauchsmuster 86 27 655. In this polymerization apparatus, a plurality of light rods, which form a light source surround a workpiece to be polymerized. A halogen lamp is provided as a heat source. In order to ensure a uniform irradiation of the workpiece to be polymerized, the workpiece is positioned on a turntable. Despite the comparatively complicated construction, the known polymerization apparatus is dissatisfactory with regard to its manipulation and its polymerization action.

Further polymerization apparatus have been suggested in which the heat loading of the workpiece to be polymerized is provided only when needed. Such a solution, however, is to a large extent subject to the operator's intuition and thus requires that the operator has sufficient experience to determine in which cases light curing can be speeded up by adding a heating step.

However, especially for the manufacture of dental replacement parts with light polymerization, it is important that the required curing times are adhered to because otherwise there is the risk that residual monomer remains within the dental replacement part and the polymerization degree of the cured material is unsatisfactory. In this context it is especially disadvantageous that due to the heating of the workpiece after completion of the polymerization cycle the workpiece is still too warm in order to be directly handled so that the operator has the tendency not to use the heat source. However, in borderline cases this can easily result in mix ups especially since the polymerization time for curing only by light exposure is, in general, greater than by using additionally heat polymerization.

It is therefore an object of the present invention to provide a polymerization device of the aforementioned kind that ensures fast polymerization cycles without running the risk of having insufficiently polymerized workpieces, especially in the case of dental replacement parts, whereby the manipulation should be improved and post-polymerization steps of the material are no longer needed.

SUMMARY OF THE INVENTION

A polymerization apparatus according to the present invention is primarily characterized by:

a support plate for supporting a workpiece;

a hood comprising a light source for guiding light to the workpiece, such that the light impinges on at least two sides of the workpiece;

the hood liftable relative to the support plate, so as to allow access to the workpiece when in a lifted position;

a heat source for heating the workpiece; and a control device for controlling the polymerization apparatus.

Preferably, the heat sources integrated into the hood.

The light source comprises preferably a plurality of light rods extending vertically within the hood and surrounding the workpiece when the hood is in a lowered position.

Preferably, the light rods are fluorescent tubes or gas-filled tubes.

Advantageously, the heat source comprises a plurality of heating rods positioned vertically so as to surround the workpiece.

The heat source preferably comprises three heating rods.

The polymerization apparatus may further comprise a frame to which the support plate is connected, wherein the hood is pivotably connected to the frame so as to be weight-compensated. The hood is locked in a lowered position during a polymerization cycle.

The hood preferably surrounds a light chamber enclosing the light source and the heat source and having an inner diameter that is greater than the workpiece; the light chamber preferably has inner walls completely covered with a reflective surface.

The reflective surface is preferably a polished metal surface, especially an aluminum surface.

The control device comprises a sensor, integrated into the light chamber, for detecting the luminous power within the light chamber.

The control device comprises a starter switch, coupled to the movement of the hood during lowering of the hood, for initiating a polymerization cycle.

The hood has venting slots for cooling the light source.

The light source comprises a plurality of light rods extending vertically within the hood and surrounding the workpiece when the hood is in a lowered position, wherein the venting slots are positioned above or adjacent to the light rods.

Advantageously the present invention also relates to a method of controlling the polymerization apparatus. The method for controlling a polymerization apparatus for polymerizing a workpiece, wherein the workpiece is subjected to light of a light source and heatable by a heat source, wherein light and heat are controlled with a control device in conjunction with a polymerization cycle, in which the light source is switched on at the beginning of the polymerization cycle, is inventively comprised of the following steps:

heating the workpiece to a desired temperature after switching on light source;

maintaining the desired temperature for a desired polymerization cycle time period;

subsequently shutting down the light source and the heat source for a final polymerization cycle time period.

The method further comprises the step of dividing the polymerization cycle into time periods of identical length.

In a first and second one of the time periods only the light source is switched on, in a third one of the time periods the light source and the heat source are switched on, in a fourth one of the time periods the light source is switched on and the desired temperature is maintained and controlled by the heat source, and in a fifth one of the time periods the light source and the heat source are switched off.

The time periods last approximately five minutes.

The control device has different programs for controlling the polymerization cycle, wherein one of the programs switches on the light source for two of the time periods while the heat source is switched off.

The control device comprises a programming unit for programming a sequence of switching periods for the light source and the heat source, wherein the switching periods are directly set for the light source and the heat source.

The method further includes the steps of switching the light source to full output and controlling the heat source by feedback to generate a constant elevated temperature of approximately 60° C.

The present invention also relates to a polymerization apparatus comprising a light source, a heat source, and a control device for a program-controlled switching of the heat source during a polymerization cycle.

The inventive embodiment of the polymerization apparatus includes the integration of the light source into a hood. The hood can be placed over a workpiece and can be lifted away from the workpiece.

In this embodiment an especially intensive light curing with a short polymerization cycle is possible when the light source not only extends relatively close to the workpiece, but when the annular wall of the hood together with the upper and the under side is provided with a reflective surface.

It is especially favorable when the light source is comprised of light rods which are arranged in a circular pattern on an inner diameter which is greater than the size (maximum width) of the workpiece to be hardened. It is understood that the inner diameter is to be selected for practical reasons somewhat greater in order to allow during handling a positioning tolerance of, for example, 1 cm.

Surprisingly, the inventive method in combination with the inventive polymerization apparatus provides an increased wear resistance of the end product and ensures the complete removal of residual monomer, even though inventively a post treatment by heat treatment is dispensed with.

Despite the optimal design with regard to light-technological considerations, it is not required to position the dental workpiece to be treated in a certain position on the support plate. The use of the inventive polymerization apparatus is thus very uncomplicated.

The possibility of lifting the light source together with the hood results in the advantage that the manipulation after completion of the polymerization cycle is optimized. Especially the workpiece is now accessible from all sides and cools relatively quickly and uniformly, without having to be removed from the apparatus, as is required in the prior art device described above.

According to an especially advantageous embodiment it is suggested to arrange in the area directly behind the workpiece a blower that is activated by lifting the hood at the end of the polymerization cycle, for example, for 30 seconds and cools the workpiece additionally.

According to a further especially advantageous embodiment it is suggested that the heat source is integrated into the hood in addition to the light source. Thus, the same reflectors can be used, which saves weight and material, for example, a polished aluminum surface for the light and the heat sources. Complicated filter systems such as the known cut-off filters are not needed. Furthermore, with a circular pattern of arranging the heat rods concentrically to the light rods of the light source, a uniform heat loading results which ensures a uniform radiation loading for optimizing the polymerization.

It is especially advantageous that, by lifting the workpiece from the support plate, the workpiece can be freely displaced onto a work area adjacent to or surrounding the support plate which can be a unitary part of the support plate. The workpiece can be moved to the side even before complete cooling has taken place without having to touch the plastic material, and the next workpiece to be treated can be placed onto the working area from the opposite side.

It is furthermore especially advantageous when the inventive hood is attached to a lifting and pivoting device connected to the frame of the polymerization device. With such a lifting and pivoting device the hood can be vertically effectively lifted whereby the subsequent pivot movement, following the lifting movement, allows free access to the workpiece, even from a position substantially vertically above the support plate. This is favorable in regard to the ergonomic use of the polymerization apparatus. It is especially advantageous in this context that the relatively hot heat source which serves for heating the workpiece, is outside of the reach of the operator and is far removed from the workpiece when the hood is in its uppermost lifted and pivoted position.

According to an advantageous embodiment it is suggested to support the movement of the hood by a known gas pressure spring (pneumatic spring) which serves as a weight compensation for the hood. Furthermore, an electric and program-controlled control device can be provided which, after completion of the polymerization cycle, automatically lifts the hood and brings it into the uppermost pivot position. On the other hand, it is possible to start the selected program by mechanically closing the hood against the resistance of the gas pressure spring which simplifies operation of the device.

Inventively, a special control for the light source is provided which optimizes the polymerization and especially the polymerization cycle with respect to efficiency as well as operation.

Surprisingly, the inventive sequence of one or two exclusively for irradiation, a subsequent heating time period, a temperature maintaining time period, and a final resting time period, with the light and heat sources shut off, results in an especially effective combined light-curing and heat-curing polymerization which is free of disturbances by the operator. The workpiece at the end of the polymerization cycle is already cooled so that, depending on the selection of the time period length, it can be transported without risk.

The controlled polymerization with the steps light polymerization, waiting period, switching on the heat, cooling without light and heat, results in a optimally polymerized workpiece of high wear resistance that does not require any post polymerization treatment. In addition, the stress load between metal crown and plastic is minimal and, surprisingly, gap formation is prevented.

According to an alternative embodiment it is suggested to embody the support plate as a substantially flat support plate to be placed on a support surface. This improves the positioning of the device.

According to a further embodiment it is suggested to embody the support plate in the form of an aluminum foil that is not connected to the apparatus and is freely moveable. It reflects the radiation of the light source and heat source whereby, however, a free movement, especially the movement of the workpiece that has not been completely cooled together with the aluminum foil, is provided.

BRIEF DESCRIPTION OF THE DRAWINGS

The object and advantages of the present invention will appear more clearly from the following specification in conjunction with the accompanying drawings, in which.

DESCRIPTION OF PREFERRED EMBODIMENTS

The present invention will now be described in detail with the aid of several specific embodiments utilizing FIGS. 1 and 2.

Figure 1:
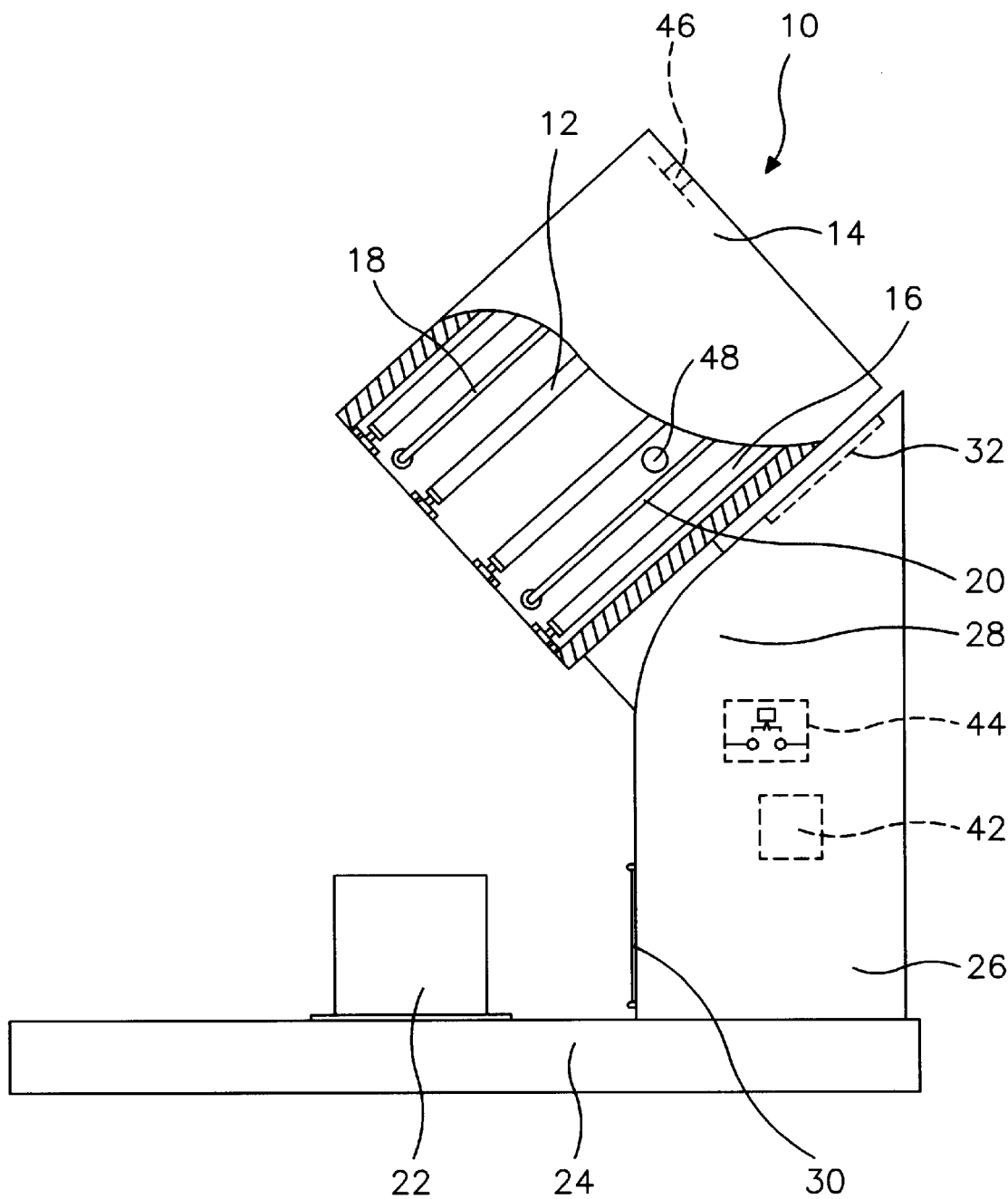
FIG. 1 is a part sectional side view of the inventive polymerization apparatus with the hood in the pivoted position.

The polymerization apparatus 10 represented in FIG. 1 comprises a light source 12 with a plurality of light rod 16 distributed about the circumference of a hood 14 as well as a heat source 18 with heat rods 20 distributed about the circumference of the hood 14. The light rods 16 limit visible light with optionally minimal UV radiation proportion and are provided to irradiate a workpiece 22 when the hood 14 is closed. The workpiece 22 is arranged on a support plate 24 which, in the shown embodiment, is fixedly connected to the frame 26 of the apparatus 10. The frame 26 also supports a lifting and pivot bearing 28 of the polymerization apparatus for lifting and guiding the hood 14. The frame 26 furthermore comprises a blower 30 that has a double function. When the hood 14 is closed, the blower 30 serves for cooling the light rods 16 which are in the form of gas-filled tubes. For this purpose, venting slots 46, one of which is shown in FIG. 1, are provided behind the gas filled tubes, which slots extend substantially vertically, and which guide cooling air from the blower directly to the light rods 16. A non-represented annular channel serves as a connection between the pressure socket of the blower and the venting slots for the light rods 16.

In the open state of the device, in which the hood 14 allows access to the workpiece 22, the blower 30 serves to cool the workpiece 22 with cooling air in order to speed up the cooling process. It is understood that a corresponding through opening for the cooling air supply to the hood 14 is provided.

In the represented embodiment according to FIG. 1, the support plate 24 is of such a size that the workpiece 22 can be freely displaced thereon and can remain in a position adjacent to the hood 14 when it is closed. This allows for a delay-free operation with a plurality of workpieces, whereby one workpiece is allowed to cool in a rest position adjacent to the hood while the next workpiece is already undergoing polymerization.

The wall area of the hood 14 surrounding the light source 12 and the heat source 18 is comprised of highly polished aluminum in order to provide a reflective surface. The same is true for the cover wall of the hood 14 and for the support plate 24. The cover wall is provided with a sensor 48 for detecting the luminous power. The sensor will activate via the control device 42 of the polymerization apparatus a warning signal when the emitted luminous power falls below a standard value. In this manner it is possible with simple means to determine whether all light rods 16 operate at full output or whether one is failing or has a light output that is too low.

The non-represented control device has furthermore an operating field 32 which is provided adjacent to the hood 14. The operating field 32 comprises keys for adjusting the luminous power so that, depending on the material to be polymerized, the luminous power can be adjusted. Furthermore, the operating field 32 allows program selection for the polymerization apparatus. The field 32 is interconnected with the control device 42.

The inventive control device initiates switching on the light source 12 at the beginning of the polymerization cycle. The manual closure of the hood 14 begins the polymerization cycle and switches on the light source 12 via switch 44. After 10 minutes, the heat source 18 is also switched on whereby heating for a time period of 5 minutes takes place. For a time period of additional 5 minutes, the temperature is maintained. Subsequently, the heat source and the light source 12 are switched off. Then, a five minute cooling phase takes place which ends the polymerization cycle. This program can be selected via the operating field 32, whereby it is understood that the exact time periods, which can be preset, can be selected according to respective requirements.

According to a further program that is usable universally for all light curing materials, the light source 12 is switched on for ten minutes whereby the heat source 18 is not switched on.

According to two further programs it is suggested that the operator can adjust the switching time periods for the light source 12 and the heating source 18, depending on the respective requirement, and can program the polymerization cycle accordingly.

Figure 2:
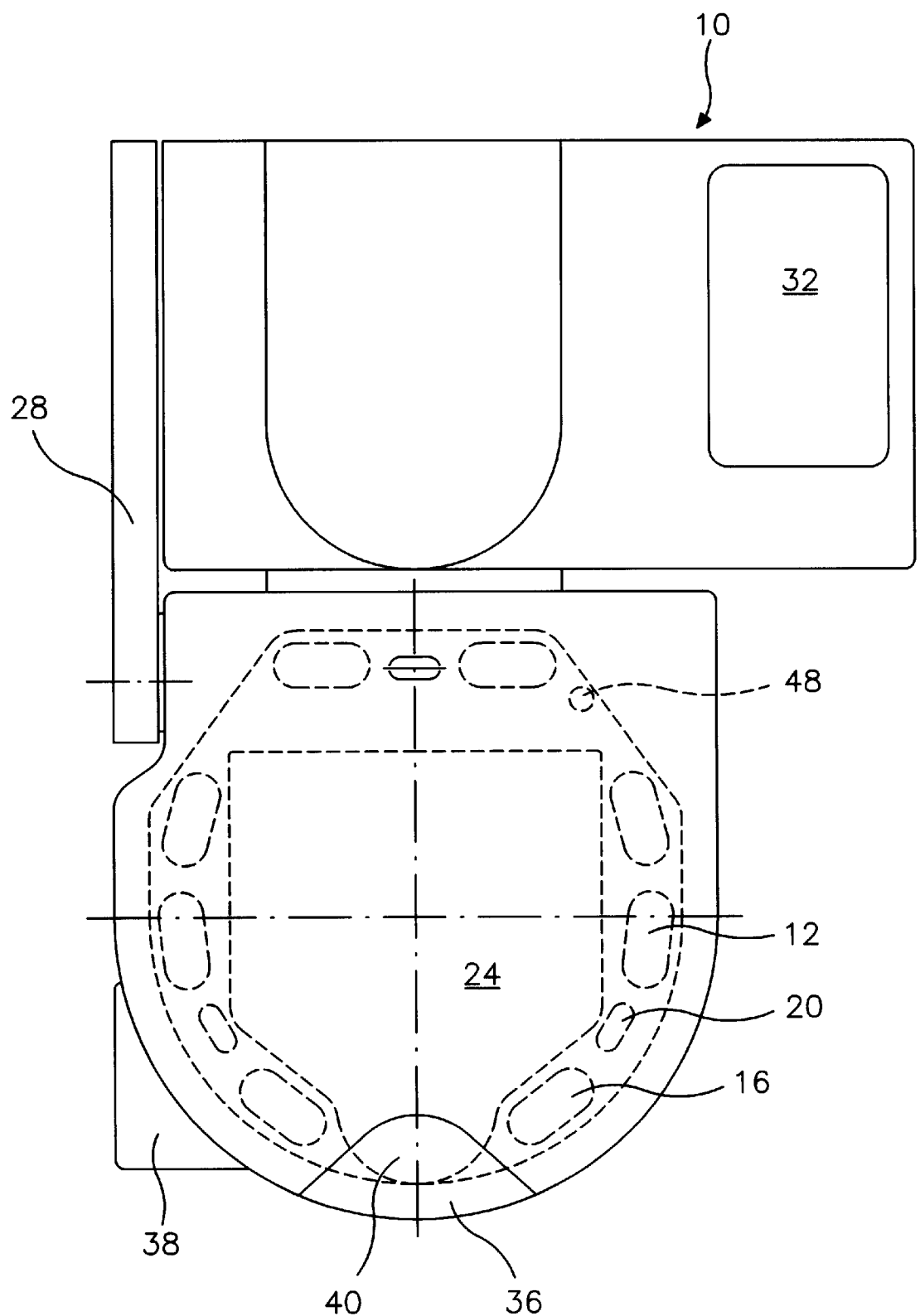
FIG. 2 is a plan view of a modified embodiment of the inventive polymerization apparatus.

A further embodiment of the inventive polymerization device is shown in FIG. 2. In this embodiment, eight light rods 16 are arranged in a circular pattern and are substantially uniformly distributed within the hood 14. Furthermore, three heat rods 20 are also arranged in a circular pattern uniformly distributed within the hood 14. The pivot bearing 28 is provided at one side and guides with a gas pressure spring (pneumatic spring) the hood 14. The pressure socket 36 of the blower 30 guides cooling air to the light rod 16. In a cutout 36 of the hood 14 a non-represented port is provided. The light source 12 can be operated with reduced luminous power in order to allow a visual control of the introduced workpiece 22 even when the hood 14 is closed. Laterally to the hood 14 a grip 38 is provided thereat which serves for adjusting the pivoting and lifting position of the hood 14. The support plate 24 has a special design with a projection 40 facing toward the front side of the apparatus. The light rods 16 are fastened only at one end and are suspended from above from their securing points. This facilitates their exchange.

The present invention is, of course, in no way restricted to the specific disclosure of the specification and drawings, but also encompasses any modifications within the scope of the appended claims.

What is claimed is:

1. A polymerization apparatus comprising:
   a frame;
   a support plate mounted on the frame for supporting a workpiece;
   a hood in the form of a dome mounted on the frame for movement between lifted and lowered positions, and which will, in its lowered position, surround the sides and top of a workpiece, and which will, when in its lifted position, allow access to the workpiece; the hood being provided with a light source for guiding light to the workpiece such that the light impinges on at least two sides of the workpiece when the hood is in its lowered position;
   a heat source carried by the hood for heating the workpiece; and
   a control device for controlling said polymerization apparatus.

2. A polymerization apparatus according to claim 1, wherein said light source comprises a plurality of light rods extending vertically within said hood and surrounding the workpiece when said hood is in a lowered position.

3. A polymerization apparatus according to claim 2, wherein said light rods are selected from a group consisting of fluorescent tubes and gas-filled tubes.

4. A polymerization apparatus according to claim 1, wherein said heat source comprises a plurality of heating rods extending vertically within said hood so as to surround the workpiece.

5. A polymerization apparatus according to claim 1, wherein said heat source comprises three heating rods.

6. A polymerization apparatus according to claim 1, wherein said hood is pivotably connected to said frame so as to be weight-compensated, said hood being locked in a lowered position during a polymerization cycle.

7. A polymerization apparatus according to claim 1, wherein said hood surrounds said light source and said heat source and has an inner diameter that is greater than the workpiece, wherein said hood has inner walls completely covered with a reflective surface.

8. A polymerization apparatus according to claim 7, wherein said reflective surface is a polished metal surface.

9. A polymerization apparatus according to claim 8, wherein said metal surface is aluminum.

10. A polymerization apparatus according to claim 7, wherein said control device includes a sensor, integrated into said hood for detecting the luminous power within said hood.

11. A polymerization apparatus according to claim 1, wherein said control device includes a starter switch mounted on said frame and coupled to a movement of said hood during lowering of said hood for initiating a polymerization cycle.

12. A polymerization apparatus according to claim 1, wherein said hood has venting slots for cooling said light source.

13. A polymerization apparatus according to claim 12, wherein said light source comprises a plurality of light rods extending vertically within said hood and surrounding the workpiece when said hood is in a lowered position, wherein said venting slots are positioned above and adjacent to said light rods.

14. A method of controlling a polymerization apparatus for polymerizing a workpiece, wherein the workpiece is subjected to light of a light source and is heatable by a heat source wherein light and heat are controlled with a control device in conjunction with a polymerization cycle, in which the light source is switched on at the beginning of the polymerization cycle, said method comprising the steps of:

providing an apparatus including separate light and heat sources;

heating the workpiece to a desired temperature after switching on said light source;

maintaining the desired temperature for a desired polymerization cycle time period; and subsequently shutting down said light source and said heat source for a final polymerization cycle time period.

15. A method according to claim 14, further comprising the step of dividing the polymerization cycle into time periods of identical length.

16. A method according to claim 15, wherein in a first and second one of the time periods only said light source is switched on, wherein in a third one of the time periods said light source and said heat source are switched on, wherein in a fourth one of the time periods said light source is switched on and the desired temperature is maintained and controlled by said heat source, and in a fifth one of the time periods said light source and said heat source are switched off.

17. A method according to claim 15, wherein the time periods last approximately five minutes.

18. A method according to claim 15, wherein the control device has different programs for controlling the polymerization cycle, wherein one of the programs switches on said light source for two of the time periods while said heat source is switched off.

19. A method according to claim 14, wherein the control device comprises a programming unit for programming a sequence of switching periods for said light source and said heat source, wherein said switching periods are directly set for said light source and said heat source.

20. A method according to claim 14, further comprising the steps of switching said light source to full output and controlling said heat source by feedback to generate a constant elevated temperature of approximately 60° C.

* * * * *